(12) United States Patent
Trimmer

(10) Patent No.: US 8,734,523 B2
(45) Date of Patent: May 27, 2014

(54) LIMITED MOTION TIBIAL BEARING

(75) Inventor: Kenneth Trimmer, Waldwick, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 23 days.

(21) Appl. No.: 13/484,652

(22) Filed: May 31, 2012

(65) Prior Publication Data

US 2013/0325137 A1    Dec. 5, 2013

(51) Int. Cl.
*A61F 2/38* (2006.01)

(52) U.S. Cl.
USPC ..................................... 623/20.33

(58) Field of Classification Search
USPC ................. 623/20.21, 20.28, 20.32, 20.33
See application file for complete search history.

(56) References Cited

U.S. PATENT DOCUMENTS

| | | |
|---|---|---|
| 4,673,407 A | 6/1987 | Martin |
| 4,795,468 A | 1/1989 | Hodorek et al. |
| 5,047,057 A | 9/1991 | Lawes |
| 5,080,675 A | 1/1992 | Lawes et al. |
| 5,282,866 A | 2/1994 | Cohen et al. |
| 5,387,240 A | 2/1995 | Pottenger et al. |
| 5,413,604 A | 5/1995 | Hodge |
| 5,824,104 A | 10/1998 | Tuke |
| 5,879,394 A | 3/1999 | Ashby et al. |
| 5,928,286 A | 7/1999 | Ashby et al. |
| 5,957,979 A | 9/1999 | Beckman et al. |
| 6,179,876 B1 | 1/2001 | Stamper et al. |
| 6,238,434 B1 | 5/2001 | Pappas |
| 6,258,126 B1 * | 7/2001 | Colleran ............... 623/20.29 |
| 6,296,666 B1 | 10/2001 | Gardner |
| 6,319,283 B1 | 11/2001 | Insall et al. |
| 6,413,279 B1 | 7/2002 | Metzger et al. |
| 6,428,577 B1 | 8/2002 | Evans et al. |
| 6,875,235 B2 * | 4/2005 | Ferree ................. 623/20.32 |
| 6,972,039 B2 | 12/2005 | Metzger et al. |
| 7,179,295 B2 | 2/2007 | Kovacevic |
| 7,740,662 B2 | 6/2010 | Barnett et al. |
| 2005/0209702 A1 | 9/2005 | Todd et al. |
| 2009/0088861 A1 | 4/2009 | Tuke et al. |

OTHER PUBLICATIONS www.masterbond.com, Biocompatible Adhesives, printed May 16, 2012, 2 pages.
www.masterbond.com, EP41SMed Product Description, printed Jan. 14, 2014, 1 page.
www.masterbond.com, EP42HT-2Med Product Description, printed Jan. 17, 2014, 1 page.
www.masterbond.com, EP62-1 Med Product Description, printed Nov. 17, 2014, 1 page.

* cited by examiner

*Primary Examiner* — Bruce E Snow
*Assistant Examiner* — Brian Dukert
(74) *Attorney, Agent, or Firm* — Lerner, David, Littenberg, Krumholz & Mentlik, LLP

(57) ABSTRACT

A tibial implant comprising: a baseplate having a bone contacting surface, a bearing support surface and a proximally extending wall at least partially surrounding the bearing support surface; a bearing component slidably mounted with respect to the baseplate bearing support surface, the bearing component having a proximally facing condylar surface and a distally facing surface for contacting the baseplate bearing support surface the proximally and distally facing bearing component surfaces spaced to define a circumferential side surface therebetween; and an elastic gasket element interposed within a gap formed between the baseplate proximally extending wall and the bearing component circumferential side surface.

23 Claims, 6 Drawing Sheets

LIMITED MOTION TIBIAL BEARING

BACKGROUND OF THE INVENTION

A total knee prosthesis typically comprises a tibial baseplate and a femoral component with an intervening meniscal bearing component which may have medial and lateral sides. Typically the tibial plate and femoral compartment are made from a suitable metal or metal alloy, such as an alloy of cobalt and chromium, whereas the meniscal bearing component is made from a synthetic plastic material, for example ultra high molecular weight polyethylene. In some designs the meniscal bearing component is fixed to the tibial plate. However, in others it is free to float to some extent with respect to the tibial plate in an attempt to mimic more closely the natural movement of the knee. In some arrangements the meniscal component may be allowed rotary and/or sliding motion on the tibial baseplate. This movement may reduce the occurrences of dislocation of the components of the prosthesis in normal walking.

Examples of prior art prostheses which include some floating bearing surfaces include U.S. Pat. No. 6,972,039, U.S. Pat. No. 2005/0209702, U.S. Pat. No. 6,428,577, U.S. Pat. No. 6,413,279, U.S. Pat. No. 6,319,283, U.S. Pat. No. 6,296,666 and U.S. Pat. No. 6,238,434. Although these and other prior art prostheses offer advantages over earlier arrangements in providing certain degrees of freedom that are not present where the bearing surface is fixed to the tibial plate or is integral therewith, problems with dislocation can still occur, particularly if the ligaments salvaged and tensioned by the surgeon during the implantation of the prosthesis do not provide the required support. Further, where the meniscal component is allowed to have anterior-posterior translation motion, spinout of the bearing may occur.

With a view to increasing stability and to reducing the risks of spinout, prostheses have been suggested which include a post extending superiorly from the tibial component and which in use will be located in the inter-condylar space of the femur. However, these prostheses suffer from various disadvantages. In particular, the interaction between the surface of the post and the surface of the femoral component of the prosthesis can lead to metal wear which may lead to metal particles being released which in turn can lead to accelerated wear of any polymeric components possibly requiring early revision operations.

It is therefore desirable to provide a mobile bearing tibial implant comprising a tibial component and a meniscal component which when used together provide the desired range of motion in flexion, tension and in rotation and which overcome the problem associated with the risk of spinout noted in the prior art. It is further desirable to provide an arrangement which has non metal on metal components which would not lead to metal on metal wear.

BRIEF SUMMARY OF THE INVENTION

The limited motion tibial bearing construct of the present invention is a highly conforming (coronal and sagittal plane) UHMWPE tibial bearing surrounded by a ring or "gasket" of an elastic material, such as polyurethane or silicone elastomer. This gasket is fit into an undercut rim of a metal tibial tray or baseplate having a polished top (proximal facing) side. An ultra high molecular weight polyethylene (UHMWPE) bearing may be used which may be asymmetric, with the narrower anterior-posterior (A-P) dimension on the lateral side. This asymmetric insert is usually placed in a symmetric tray so that there will be a gap around the insert varying from smaller, around the medial side and growing larger around the narrowed lateral side. This gap is filled by the flexible gasket. The gasket will allow limited motion of the UHMWPE bearing based on its elasticity and the size of the gap between the rim of the metal tray and the walls of the tibial bearing. It is also possible to have separate medial and lateral bearing elements.

The condylar surface of the UHMWPE tibial bearing closely matches the femoral component in the coronal and sagittal planes. This geometry has the benefit of maximizing contact area and minimizing contact stress. The consequences of this are having the transfer of load through the insert and to the insert to bearing locking mechanisms as well as to the bone to implant interface. Previous attempts to maintain high conformity while reducing implant to implant and implant to bone stresses resulted in the development of the mobile bearing knees. These designs allowed for, at a minimum, rotation of the bearing on the tibial tray up to almost no constraint of motion between the tibial bearing and the tibial tray. As a result most or the entire rotational and translational load of the knee is absorbed by the remaining soft tissue of the knee. The present invention is intended to share the load by allowing limited anterior posterior translation and internal external rotation of the femoral component with respect to the tibial bearing through the use of a deformable gasket.

In normal knee kinematics, the torque versus rotation shows a gradual increase in the torque required to rotate the knee until the point is reached where the surrounding soft tissues are tensioned and the natural flexibility of the meniscus has reached its limit. At that point, the torque increases rapidly. When looking at rotating platform or mobile bearing knees, the torque required to rotate the knee is relatively minimal until the ligaments are abruptly tensioned.

A similar phenomenon is displayed when looking at load versus anterior posterior translation at various degrees of flexion.

The goal of the elastic gasket around the tibial insert is to provide increased resistance to anterior and posterior motion and internal-external rotation as the motion increases. The spring constant of the elastic material as well as its thickness determines the stiffness of the gasket. The stiffness determines the limits of motion between the tibial bearing and the tibial tray as well as determines the load transfer between the implant interfaces and the implant to bone interface. This also assists in load sharing with the soft tissues. As the motion of the insert increases, the load being taken up by the soft tissue will also gradually increase.

The limited motion tibial bearing insert of the present invention is implanted in the same manner as current fixed bearing tibial inserts. The insert configurations could be used in both cruciate retaining situations as well as a PCL substituting as the anterior lipping of the insert and high level of conformity of the femoro-tibial articulation provides A-P stability.

The present invention is optimized when used with a femoral component with a single A-P radius as this would maximize conformity in the sagittal plane thereby maximizing contact area and minimizing contact stresses.

The tibial bearings are made in multiple thicknesses as well as multiple outer profiles, allowing for a greater amount of elastic material between the metal tray and the bearing, which facilitates different amounts of translation and rotation of the bearing to accommodate individual patients' ligament stability.

One aspect of a tibial implant of the present invention has a baseplate with a bone contacting surface, a bearing support surface and a proximally extending wall at least partially surrounding the bearing support surface. A bearing component is slidably mounted with respect to the baseplate bearing support surface. The bearing component has a proximally facing condylar surface and a distally facing surface for contacting the baseplate bearing support surface. The proximally and distally facing bearing component surfaces are spaced to define a circumferential side surface or wall therebetween. An elastic gasket element is interposed within a gap formed between the baseplate proximally extending wall and the bearing component circumferential side surface.

The baseplate proximally extending wall extends around a periphery of the bearing support surface. The bearing component preferably is one-piece with an anterior-posterior dimension of the bearing component being less on a lateral side thereof than on a medial side thereof. The bearing component could also be in two pieces (lateral and medial) or the gasket could also be used in a unicondylar knee replacement. The gap between the baseplate proximally extending wall and the bearing component side surface is smaller around the medial side of the bearing component than on the lateral side of the bearing component which has the lesser anterior-posterior dimension. The gap is at least partially filled with the elastic gasket. The elastic gasket extends around the periphery of the proximally extending wall and has a thickness along a plane parallel to the baseplate bearing contact surface which is greater on a lateral side of the bearing support surface. Preferably the elastic gasket is thickest on a posterior side of the lateral side of the bearing contact surface. The elastic gasket may be polyurethane or silicone rubber having a predetermined spring constant. The gasket thickness and spring constant combine to produce a stiffness which restricts movement of the bearing component under physiological loading. The bearing component is preferably a one piece component having medial and lateral condylar portions.

Another aspect of the present invention may have a tibial component with a baseplate having a bone contacting surface, a bearing support surface and a proximally extending wall around a circumference of the bearing support surface. A gasket plate having an elastic gasket fixed to a first side thereof is provided and an opposite second side for contacting the bearing support surface of the baseplate. The gasket defines an inner wall extending proximally from the first side of the gasket plate. A bearing component is provided which has a distal surface slidably mounted on the first side of the gasket plate intermediate the inner wall of the circumferential gasket. The bearing component has a proximally facing condylar bearing portion for engaging a femoral component spaced from the bearing distal surface to define an outer wall, the outer wall of the bearing component is spaced from the inner wall of the gasket. The inner wall of the gasket includes a protrusion for engaging a groove formed in the outer wall of the bearing component. The proximally extending wall of the baseplate has a groove formed therein adjacent the bearing support surface for receiving a peripheral edge of the gasket plate. The tibial bearing component may include independent medial and lateral condylar bearing portions. The baseplate proximally extending wall may extend around an entire periphery of the baseplate or may extend around only a portion thereof. An anterior-posterior dimension of the lateral bearing portion is preferably less than an anterior-posterior dimension of the medial bearing portion. Preferably the gap between the baseplate proximally extending wall and the bearing component outer wall is smaller around the medial bearing portion than the lateral bearing portion which has the lesser anterior-posterior dimension. The gap is at least partially filled with the elastic gasket. The elastic gasket may extend around the entire circumference of the tibial component defined by the proximally extending wall and has a greater thickness along a plane parallel to the baseplate bearing contact surface on a lateral side of the baseplate.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

DETAILED DESCRIPTION

Figure 1:
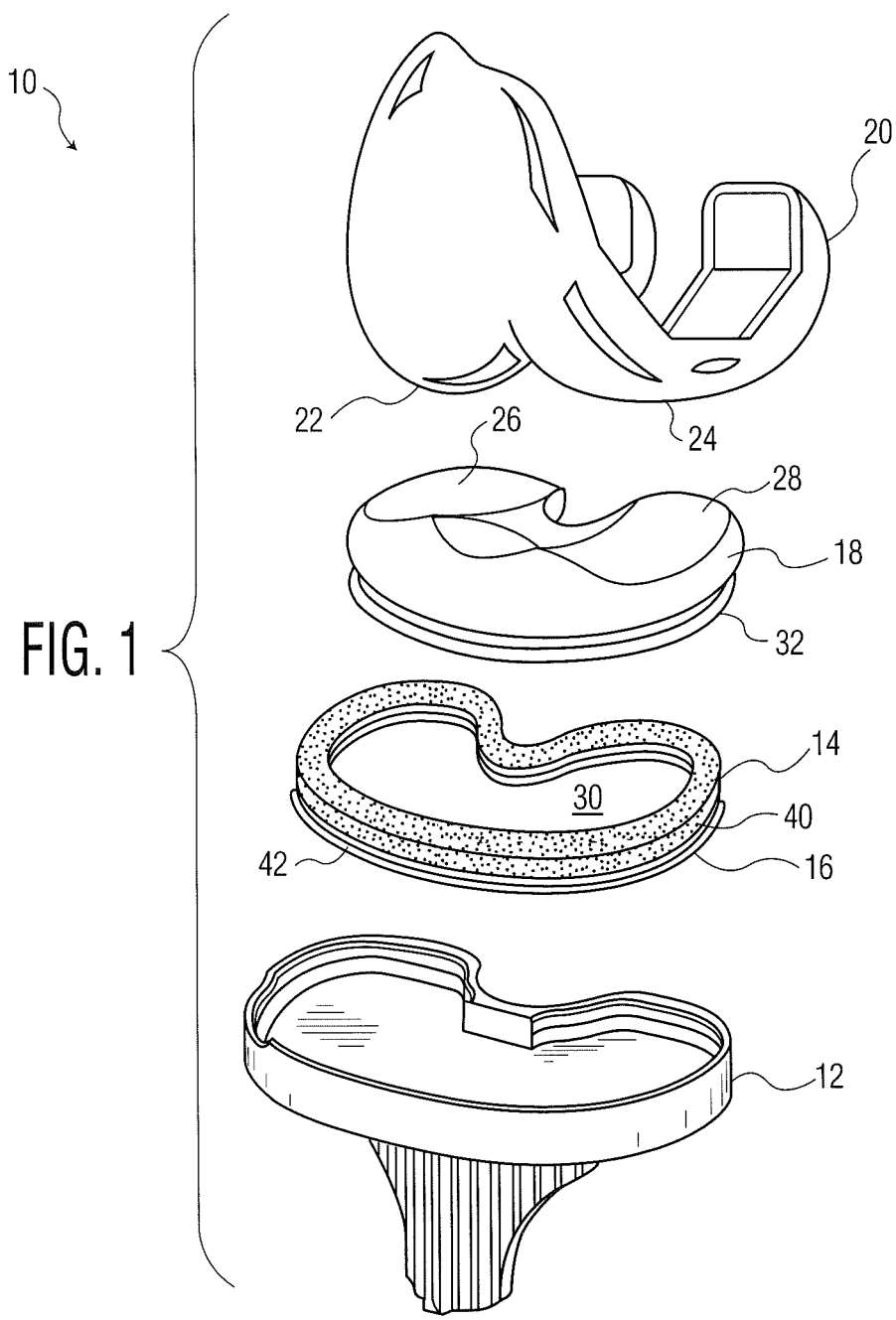
FIG. 1 is an exploded view of a total knee implant system including the limited motion tibial bearing of the present invention.

Referring to FIG. 1 there is shown an exploded view of a total knee system generally denoted as 10 composed of a tibial baseplate 12, a gasket 14 which may be mounted on a plate 16, a bearing component 18 and a femoral component 20 condyles 22 and 24 which engage the corresponding medial and lateral condyles 26 and 28 of bearing component 18. In the preferred embodiment plate 16 is bonded to gasket 14 with the intermediate proximally facing area 30 being a polished metal surface. This allows the bottom surface 32 of ultra-high molecular weight polyethylene bearing component 18 to easily slide thereon.

Figure 2:
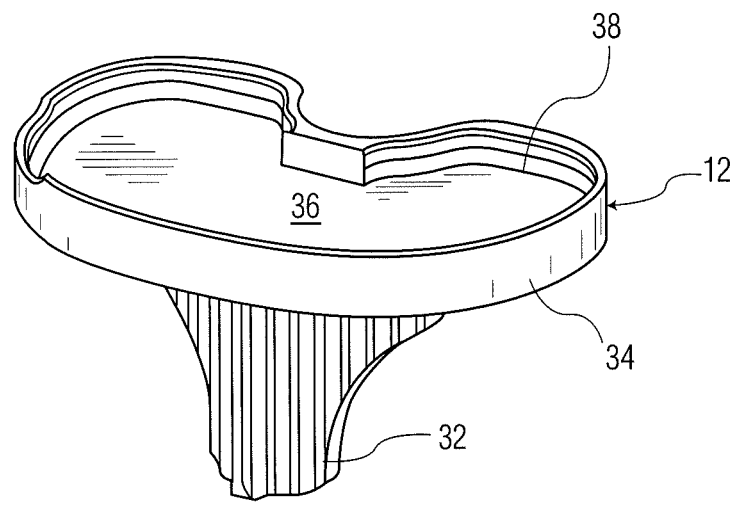
FIG. 2 is an isometric view of the tibial baseplate shown in FIG. 1.
Figure 3:
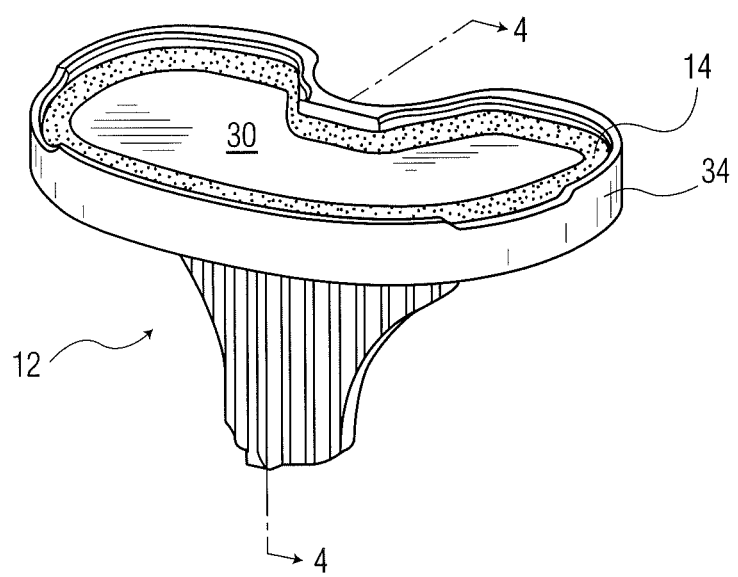
FIG. 3 is the baseplate shown in FIG. 2 including the gasket element shown in FIG. 1 mounted thereon.

Referring to FIG. 2 there is shown to be a baseplate 12 having a keel 32 for implantation into a pair of proximal tibia and having a side wall 34 extending proximally from a planar baseplate surface 36. The interior of wall 34 includes a groove 38 for receiving a portion of plate 16 which extends beyond a sidewall 40 of gasket 14. This extension portion 42 has a thickness designed to engage groove 38 and maintain the gasket/plate 16 on surface 36. Referring to FIG. 3 there is shown baseplate 12 with gasket 14 and plate 16 located within cavity 36. Thus now proximally facing 30 is located to receive bearing element 18.

Figure 4:
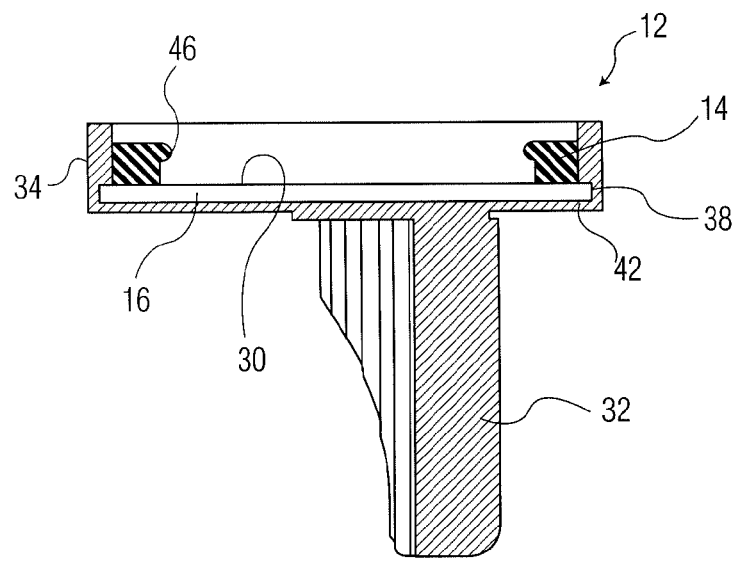
FIG. 4 is a cross-sectional view of the baseplate and gasket of FIG. 3 along lines 4-4.

Referring to FIG. 4, there is shown a cross-section of FIG. 3 along lines 4-4 with the gasket 14 and plate 16 located on surface 36 with plate extension 42 inserted into groove 38. Plate 16 has sufficient flexibility to allow this assembly to occur. As can be seen in FIG. 4 gasket 14 includes an extension 46 adapted to engage a groove around the outer circumference of the bearing component 18 to retain it in the tibial tray.

Figure 5:
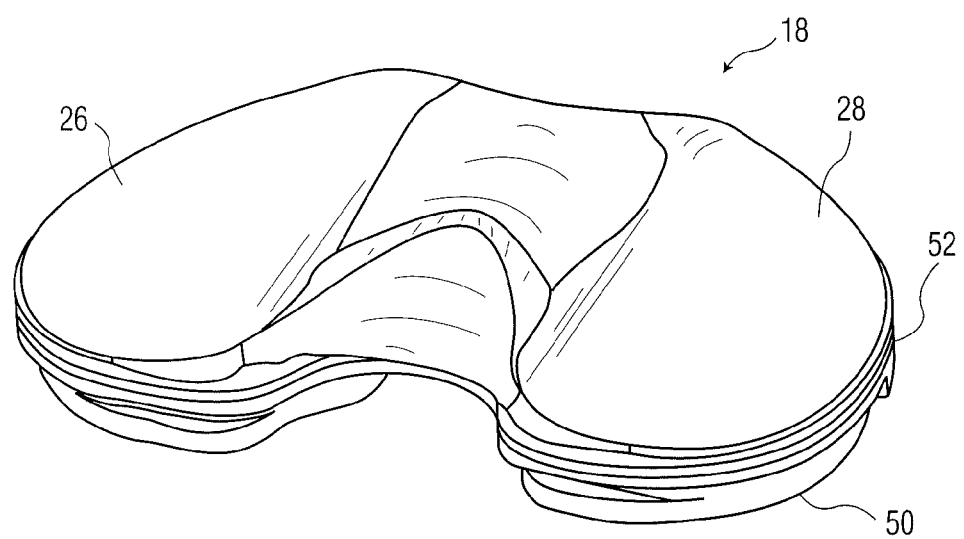
FIG. 5 is an isometric view from above of the bearing component shown in FIG. 1.

Referring to FIG. 5 there is shown a bearing component preferably made of ultra-high molecular weight polyethylene having both medial and lateral condyles 26, 28 respectively. The bearing component 18 has a smooth distally facing surface 50 and a groove 52 thereon adapted to receive protrusion 46 on gasket 14. The bearing 18 may be of any well known design including a bearing/tibial tray or baseplate combination designed for a cruise ship retaining application which typically has a posterior recess formed in both the baseplate and bearing. In addition, while a one-piece medial and lateral condylar bearing component 18 is shown the medial and lateral condyles can be located on separate ultra-high molecular weight polyethylene bearing elements mounted in a tibial baseplate or tray having a central raised area. In this design two separate gasket elements and corresponding plates can be utilized on the medial and lateral sides of the tibial tray. In addition, the concept set forth herein can be used in a unicondylar application in which only one condyle of a patient's knee is resurfaced.

Figure 6:
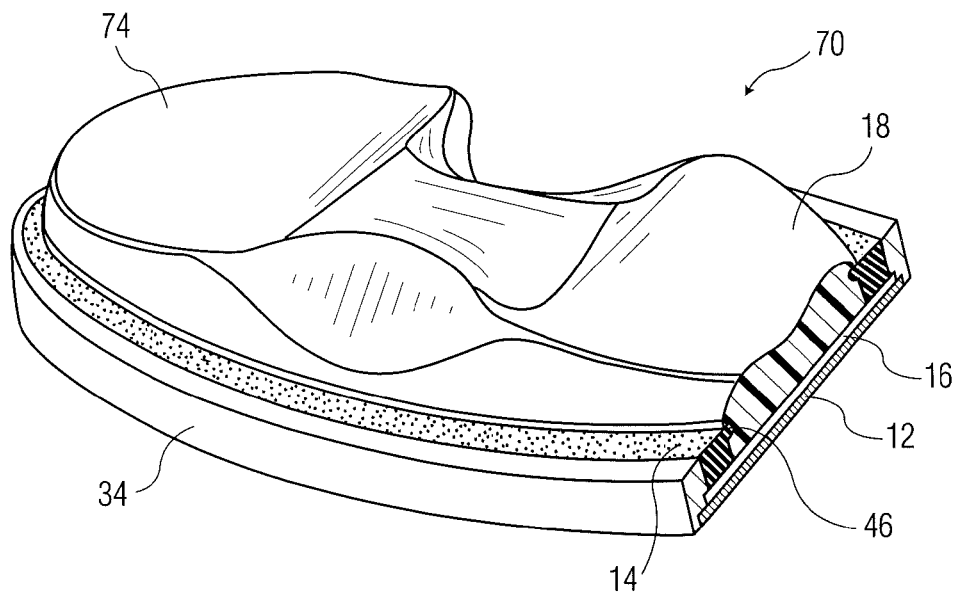
FIG. 6 is the bearing component of FIG. 5 surrounded by the gasket.
Figure 7:
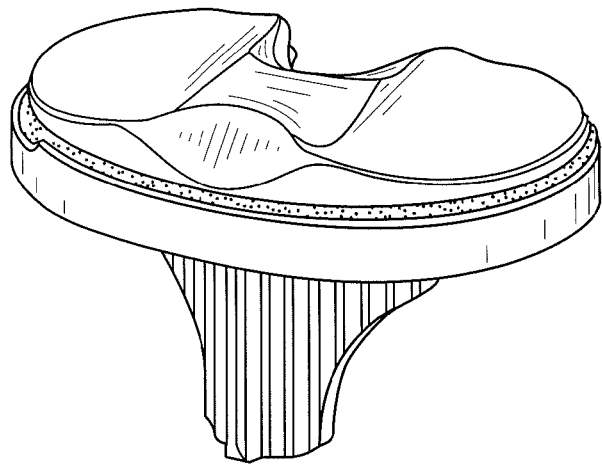
FIG. 7 is an isometric view of the assembled bearing component gasket and baseplate of FIG. 1.

Referring to FIG. 6 there is shown a partially cut away view of the tibial bearing 18 mounted showing the assembled bearing 18, gasket 14, gasket plate 16 and baseplate 12 partially and cut away. Referring to FIG. 7 there is shown the tibial implant made up of components 12, 14, 16 and 18.

Figure 8:
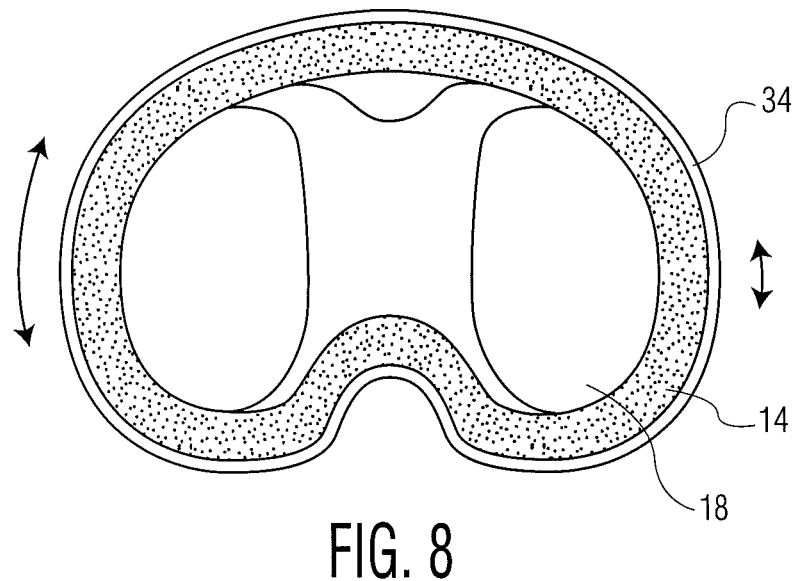
FIG. 8 is a top view of the assembly of FIG. 7.

Referring to FIG. 8 there is a top view of the assembly of FIG. 7 showing sidewall 34 of baseplate 12 gasket 14 and bearing component 11 which may move on surface 30 of plate 16 under physiologic loading. As discussed above, the movement can be varied by varying the stiffness of the material of gasket 14.

Figure 8A:
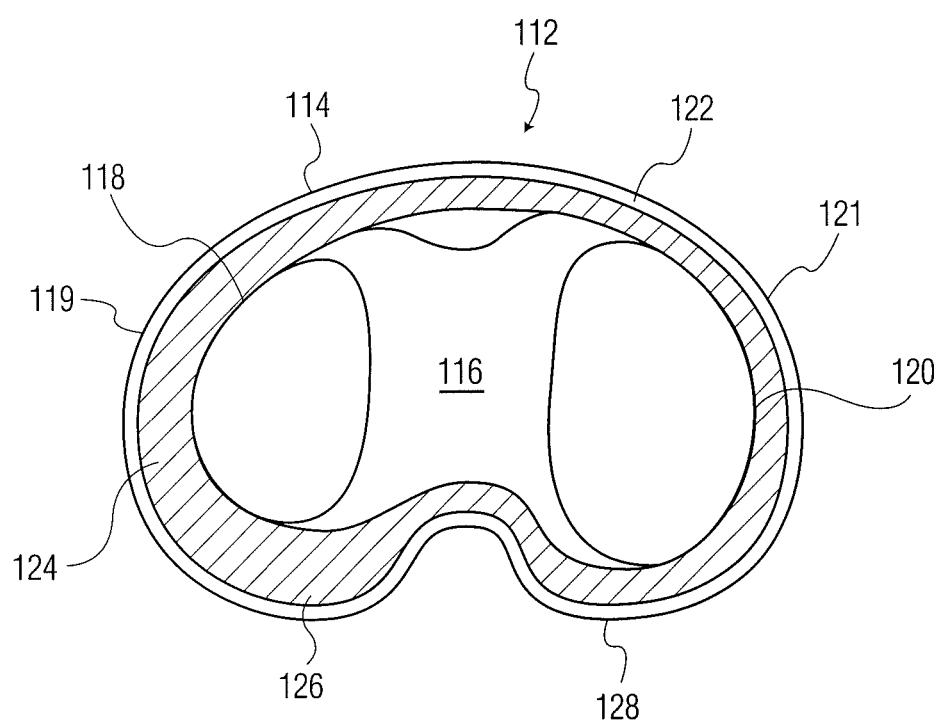
FIG. 8A is a top view of an alternate embodiment.

FIG. 8A is a top view of an alternate embodiment of the tibial baseplate construction shown in FIG. 1 and generally denoted as 112. Construction 112 has a baseplate component 114, a bearing component 116 which is mounted on a baseplate bearing contact surface similar to surface 30 of baseplate 12. The bearing component 116 has a lateral side 118 and a medial side 120. The baseplate has a lateral side 119 and a medial side 121. The gap between a baseplate proximally extending wall 122 and bearing component 116 side surfaces 118 and 120 is smaller on the medial side 120 than on the lateral side 118. The lateral side 118 of the bearing component 116 has a smaller anterior-posterior dimension than the medial side 120. Tibial component 112 has an elastic gasket 124 that extends around the periphery of the proximally extending wall 122 and has a thickness along a plane parallel to the baseplate bearing contact surface which is greater on lateral side 18, 119 of the bearing support surface. The gasket 124 is thickest at area 126 on the posterior side 128 of the lateral side 119 of baseplate 114.

Figure 9:
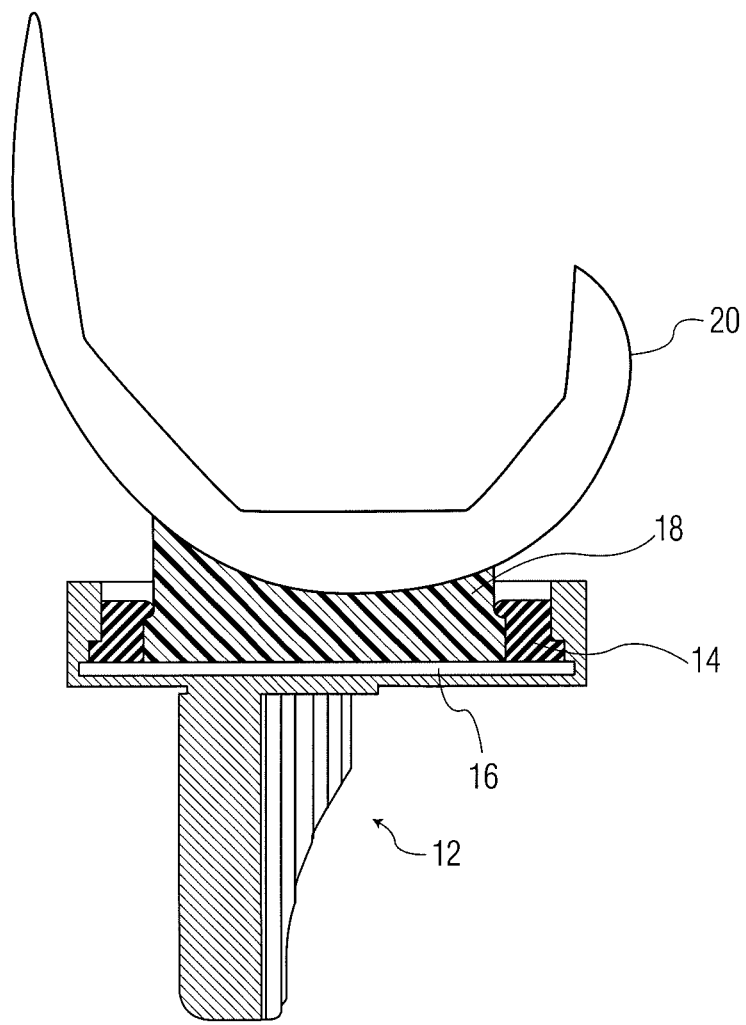
FIG. 9 is a cross-sectional view of the assembly of the tibia baseplate, gasket, bearing and femoral component.

Referring to FIG. 9 there is shown a complete assembly of the total knee implant system of the present invention with baseplate 12, gasket 14 and bearing component 18 in cross-section. Femoral component 20 is a standard femoral component as is well known in the art.

The gasket 14 may be made from polyurethane such as Corethane 80A, Chronoflex, Tecoflex or Tecothane with a thickness sufficient to allow up to 1 mm compression. The gasket 14 may be glued to the tibial baseplate 16 using epoxy or other suitable glue. For example Masterbond® adhesives EP42HT-2 Med, EP41SMed or EP62-1 Med may be used (Master Bond Inc., 154 Hobart St., Hackensack, N.J.). Corethane® 80A urethane may be obtained from Corvita Corporation of Miami, Fla. Tecoflex® and Tecothane® urethanes may be obtained from Lubrizole Corporation of Wickiffe, Ohio. Chronoflex® urethane may be obtained from AdvanSource Biomaterials, Wilmington, Mass. Generally the gasket may be between 1 and 6 mm deep and be between 2 and 10 mm in height. However, any suitable dimensions can be used.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tibial implant comprising:
a baseplate having a bone contacting surface, a proximally facing bearing support surface extending in a plane transverse to a longitudinal axis of a tibia and a proximally extending wall at least partially surrounding the proximally facing bearing support surface;
a bearing component slidably mounted with respect to the baseplate bearing support surface, the bearing component having a proximally facing condylar surface and a distally facing surface for contacting the baseplate bearing support surface, the proximally and distally facing bearing component surfaces spaced to define a circumferential side surface therebetween the distally facing surface of the bearing component defining a smaller area than an area of the proximally facing bearing support surface so that a gap exists along the plane of the bearing support surface between an inner surface of the proximally extending wall of the baseplate and the circumferential side surface of the bearing component; and
an elastic gasket element having an inner proximally extending wall and an outer proximally extending wall interposed within the gap formed between the baseplate proximally extending wall and the bearing component circumferential side surface, the elastic gasket element outer proximally extending wall adjacent the inner surface of the baseplate proximally extending wall and the elastic gasket element inner wall adjacent the circumferential side surface of the bearing component.

2. The tibial implant as set forth in claim 1 wherein the baseplate proximally extending wall extends around a periphery of the bearing support surface.

3. The tibial component as set forth in claim 2 wherein the bearing component is one-piece with an anterior-posterior dimension of the bearing component being less on a lateral side thereof than on a medial side thereof.

4. The tibial component as set forth in claim 3 wherein the gap between the baseplate proximally extending wall and the bearing component circumferential side surface is smaller around the medial side of the bearing component than on the lateral side of the bearing component having the lesser anterior-posterior dimension.

5. The tibial component as set forth in claim 4 wherein the gap between the inner surface of the baseplate proximally extending wall and the bearing component is filled with the elastic gasket, wherein the elastic gasket is uniform around the circumferential side surface of the bearing component.

6. The tibial component as set forth in claim 5 wherein the elastic gasket extends around the periphery of the proximally extending wall and has a thickness along a plane parallel to the baseplate bearing contact surface which is greater on a lateral side of the bearing support surface.

7. The tibial component as set forth in claim 6 wherein the elastic gasket is thickest on a posterior side of the lateral side of the bearing contact surface.

8. The tibial component as set forth in claim 7 wherein the elastic gasket is polyurethane or silicone rubber having a predetermined spring constant.

9. The tibial component as set forth in claim 8 wherein the gasket thickness and spring constant combine to produce a stiffness which restricts movement of the bearing component under physiological loading.

10. The tibial component as set forth in claim 1 wherein the bearing component is a one piece component having medial and lateral condylar portions.

11. A tibial component comprising:
- a baseplate having a proximally facing bone contacting surface, a bearing support surface and a proximally extending wall around a circumference of the proximally facing bearing support surface;
- a gasket plate having an elastic gasket fixed to a proximally facing first side thereof and a distally facing second side for contacting the proximally facing bearing support surface of the baseplate, the gasket defining an inner wall extending proximally from the first side;
- a bearing component having a distal surface slidably mounted on the proximally facing first side of the gasket plate intermediate the inner wall of the circumferential gasket, the bearing component having a proximally facing condylar bearing portion for engaging a femoral component wherein the proximally facing condylar bearing portion is spaced from the bearing distal surface to define a proximally-distally extending outer wall, the proximally extending outer wall of the bearing component engageable with the inner wall of the elastic gasket.

12. The tibial component as set forth in claim 11 wherein the inner wall of the gasket includes a protrusion for engaging a groove formed in the outer wall of the bearing component.

13. The tibial component as set forth in claim 11 wherein the proximally extending wall of the baseplate has a groove formed therein adjacent the bearing support surface for receiving a peripheral edge of the gasket plate.

14. The tibial component as set forth in claim 11 wherein the tibial bearing component includes independent medial and lateral condylar bearing portions.

15. The tibial implant as set forth in claim 11 wherein the baseplate proximally extending wall extends around a periophery of the baseplate.

16. The tibial component as set forth in claim 14 wherein an anterior-posterior dimension of the lateral bearing portion is less than an anterior-posterior dimension of the medial bearing portion.

17. The tibial component as set forth in claim 16 wherein the gap between the baseplate proximally extending wall and the bearing component outer wall is smaller around the medial bearing portion than the lateral bearing portion having the lesser anterior-posterior dimension.

18. The tibial component as set forth in claim 17 wherein the gap is at least partially filled with the elastic gasket.

19. The tibial component as set forth in claim 18 wherein the elastic gasket extends around the circumference of the tibial component defined by the proximally extending wall and has a greater thickness along a plane parallel to the baseplate bearing contact surface on a lateral side of the baseplate.

20. The tibial component as set forth in claim 19 wherein the elastic gasket is thickest on a posterior side of the lateral side of the baseplate.

21. The tibial component as set forth in claim 20 wherein the elastic gasket is polyurethane or silicone rubber having a predetermined spring constant.

22. The tibial component as set forth in claim 20 wherein the gasket thickness and spring constant combine to produce a stiffness which restricts movement of the bearing component under physiological loading.

23. The tibial component as set forth in claim 1 wherein the tibial bearing component includes both medial and lateral condylar bearing portions.

* * * * *